United States Patent [19]
Klinkhammer

[11] Patent Number: 6,103,902

[45] Date of Patent: Aug. 15, 2000

[54] CARBAMOYLATION PROCESS

[75] Inventor: Uwe Klinkhammer, Eschbach, Germany

[73] Assignee: Hoffmann-La Roche Inc., Nutley, N.J.

[21] Appl. No.: 09/370,817

[22] Filed: Aug. 9, 1999

[30] Foreign Application Priority Data

Aug. 10, 1998 [EP] European Pat. Off. .............. 98114978

[51] Int. Cl.$^7$ ...................... C07D 239/02; C07D 415/00; C07D 401/00; A01N 43/54; A01K 31/505
[52] U.S. Cl. .......................... 544/319; 544/319; 544/327; 544/333; 514/256; 514/269
[58] Field of Search ..................................... 514/256, 269; 544/319, 327, 333

[56] References Cited

U.S. PATENT DOCUMENTS 6,004,965  12/1999  Breu et al. ............................... 514/256

FOREIGN PATENT DOCUMENTS

WO96/19459  6/1996  WIPO .

OTHER PUBLICATIONS

Tetrahedron; Minisci et al; vol. 41, No. 19, pp. 4157–4170 (1985).

*Primary Examiner*—Richard L. Raymond
*Assistant Examiner*—Ben Schroeder
*Attorney, Agent, or Firm*—George W. Johnson; William H. Epstein; John P. Parise

[57] ABSTRACT

The present invention is concerned with a novel process for the carbamoylation of substituted pyridines, especially with a process for the preparation of compounds of formula I

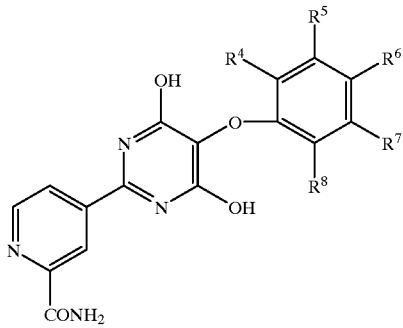

wherein $R^4$ to $R^8$ represent hydrogen, lower-alkoxy or halogen;

or optionally salts thereof.

19 Claims, No Drawings

CARBAMOYLATION PROCESS

BACKGROUND OF THE INVENTION

This application claims benefit to EP 98114978.4 filed Aug. 10, 1998.

Radical carbamoylation of basic heteroaromates has been described by F. Minisci et al. in Tetrahedron (1985), 41, 4157. The reaction disclosed therein is performed in the presence of a catalytic amount of iron(II)sulfate. However, the use of catalytic amounts of iron (II) sulfates for carbamoylation of basic heteroaromatics has proven relatively commercially unsuccessful since the carbamoylation products are not produce with high yields. Therefore, the amounts of the carbamoylation product produced by this method have been very low.

SUMMARY OF INVENTION

In accordance with this invention, we have discovered a process for the producing an amide selected from a compound of the formula

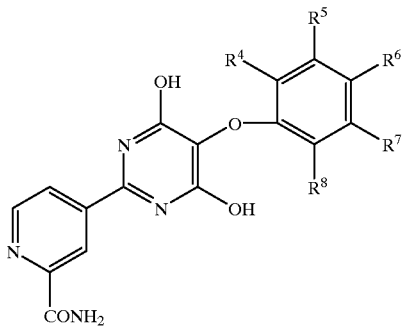

wherein $R^4$ through $R^8$ are each independently hydrogen, lower-alkoxy or halogen;
and a salt thereof by reacting a compound of the formula

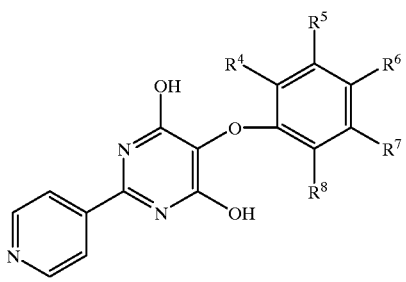

wherein $R^4$ through $R^8$ are as above;
or a salt thereof with formamide and an oxidizing agent in an aqueous acidic solution, to produce said amide, said reaction being carried out in the presence of 15 to 40 mole % of an ionic Fe (II) salt, said mole % being based upon the moles of said compound of formula II in the reaction.

Surprisingly, it has been found that when utilizing amounts of an ionic Fe (II) salt of greater than catalytic quantities which greater amounts are from 15 to 40 mole % based upon the moles of the compound of formula II in the reaction, this reaction produces compound II of formula I in high yields with outstanding conversions. It is because of the high production of the compound of formula I that a new method for converting the compounds of formula II to known pharmaceutically active tetrazoles of the formula

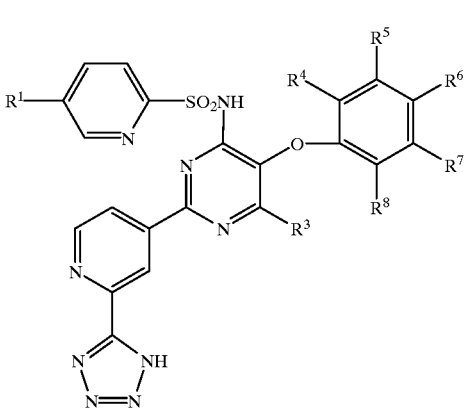

wherein
$R^1$ is lower-alkyl;
$R^3$ is —O—$(CR_aR_b)_n$—$OR^9$;
$R^4$ to $R^8$ are each individually hydrogen, lower-alkoxy or halogen;
$R^9$ is hydrogen, aryl, lower-aralkyl, heterocyclyl or a residue —C(O)NHR$^{10}$;
$R^{10}$ is lower-alkyl, phenyl, substituted phenyl, pyridyl or substituted pyridyl;
$R_a$ and $R_b$ are each independently hydrogen or lower-alkyl; and
n is 2, 3 or 4;
and salts thereof;
is achieved.

The pharmaceutically active tetrazoles of formula VI above are known endothelin receptor inhibitors which can be used for the treatment of disorders associated with endothelin receptor activities, especially circulatory disorders such as hypertension, ischaemia, vasospasms and angina pectoris.

DETAILED DESCRIPTION OF THE INVENTION

The following definitions are set forth to illustrate and define the meaning and scope of the various terms used to describe the invention herein.

The term "lower" refers to a group consisting of one to seven, preferably one to four carbon atom(s), unless otherwise indicated.

The term "lower-alkyl" refers to a branched or straight chain monovalent alkyl radical of one to seven carbon atoms, preferably one to four carbon atoms. This term is further exemplified by such radicals as methyl, ethyl, n-propyl, isopropyl, i-butyl, n-butyl, t-butyl and the like.

The term "lower-alkoxy" refers to the group —O—R', where R' is a lower-alkyl.

The term "halogen" refers to fluoro, chloro, bromo and iodo, with chloro being preferred.

The term "aryl" refers to a monovalent carbocyclic aromatic radical (e.g. phenyl), optionally substituted, independently, with halogen, lower-alkyl, lower-alkoxy, lower-alkylenedioxy, carboxy, trifluoromethyl and the like.

The term "lower-aralkyl" refers to a lower-alkyl group substituted by aryl as defined above, e.g. phenyl or substituted phenyl, preferably benzyl.

The term "heterocyclyl" refers to mono- or bicyclic, 5- and 6-membered heterocyclic rings having at least three heteroatom selected from oxygen, nitrogen and sulphur, such as 2- and 3-furyl, 2-, 4- and 5-pyrimidinyl, 2-, 3- and 4-pyridyl, 1,2- and 1,4-diazinyl, 2- and 3-thienyl, oxazolyl, thiazolyl, imidazolyl, benzofuranyl, benzothienyl, purinyl, quinolyl, isoquinolyl and quinazolyl, which residues can be substituted, e.g. by 1 or 2 lower-alkyl groups. Preferably, heterocyclyl is a pyridyl residue or a substituted pyridyl residue.

The term "substituted phenyl" refers to a phenyl group which is mono-, di- or tri-substituted, independently, with halogen, lower-alkyl, lower-alkoxy, lower-alkylenedioxy, carboxy, trifluoromethyl and the like.

The term "substituted pyridyl" refers to a pyridyl group which is mono-, di- or tri-substituted, independently, with halogen, lower-alkyl, lower-alkoxy, lower-alkylenedioxy, carboxy, trifluoromethyl and the like.

The term "lower-alkylenedioxy" refers to the group —O—(CH$_2$)$_n$—O—, wherein n is an integer of two to seven, preferably an integer of two to four.

The salts utilized herein are preferably pharmaceutically acceptable salts. These "pharmaceutically acceptable salts" include alkali salts such as Na or K salts or alkaline earth metal salts such as Ca or Mg salts or salts with amines such as monoethanolamine as well as salts with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms.

In converting the compound of formula II to the compound of formula I, compound of formula II is reacted with formamide and an oxidizing agent. This reaction takes place in an aqueous acidic solution and in the presence of an ionic Fe(II) salt. Any conventional ionic Fe(II) salt can be utilized in this reaction. The ionic Fe (II) salt can be formed with any conventional anion, preferably chloride, bromide, sulfate, phosphate, tetrafluoroborate, or hexafluoroborate anions. In carrying out this reaction, the new and unexpected results of this process are achieved by utilizing greater than catalytic amounts of this ionic Fe(II) salt. These greater amounts of this Fe(II) salt for carrying out this reaction are in the range of from 15 to 40 mole % based upon the moles of said compounds of formula II in the reaction, with an amount of ionic Fe(II) salt of from 20 to 30 mole %, based upon the moles of said compound of formula II in the reaction being especially preferred. Therefore, if one wishes to convert 100 moles of the compound of formula II to the compound of formula I, the ionic Fe(II) salt that is used should be present in the reaction mixture in an amount of from 15 to 40 moles.

In carrying out this reaction, any conventional oxidizing agent which is soluble in an aqueous acidic solution can be utilized. Among the preferred oxidizing agents is hydrogen peroxide. Any amount of said oxidizing agent sufficient to oxidize the compound of formula II can be utilized, preferably the oxidizing agent is present in an amount of from about 1.5 to 2.5 moles per mole of the compound of formula II in the reaction. In carrying out this reaction, temperature and pressure are not critical. Generally, it is preferred to carry out this reaction at a temperature of from 0° C. to 35° C., preferably at a temperature of from 0° C. to 25° C. with temperatures of 0° C. to 10° C. being especially preferred. The aqueous solution can be any aqueous solution containing an inorganic or organic acid. Generally, for organic acids, a sulfonic acid solution is preferred.

More particularly the reaction refers to the conversion of 5-(2-methoxy-phenoxy)-2-pyridine-4-yl-pyrimidine-4,6-diole to 4-[4,6-dihydroxy-5-(2-methoxy-phenoxy)-pyrimidine-2-yl]-pyridine-2-carboxylic acid amide using the reaction conditions as described above.

In accordance with this invention, the compounds of formula I can be converted to endothelin receptor inhibitors of formula VI which are described in International Patent Application WO 9619459.

The compounds of formula VI are prepared from the compound of formula I by the following steps:

The compound of formula I above is next converted into a compound of formula III

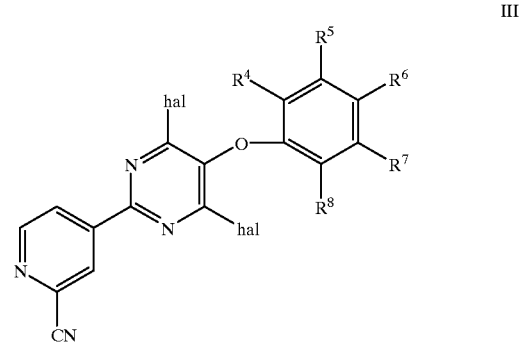

wherein
R$^4$ to R$^8$ is as above; and
hal is halogen;

or salts thereof reacting by the compound of formula I or a salt thereof with a water removing and halogenating agent. In carrying out this reaction, any halogenating agent capable of removing water can be utilized in this conversion. Among the preferred halogenating agents are PO(hal)$_3$, P(hal)$_5$, or SO(hal)$_2$. This reaction is generally carried out in the presence of a base, any organic or inorganic base can be utilized in this conversion. Examples of water removing and halogenating agents are POCl$_3$, PCl$_5$ or SOCl$_2$, preferably POCl$_3$. The reaction is preferably carried out in a basic solvent such as diisopropyl ethylamine.

The compounds of formula III above may be converted into compounds of formula IV

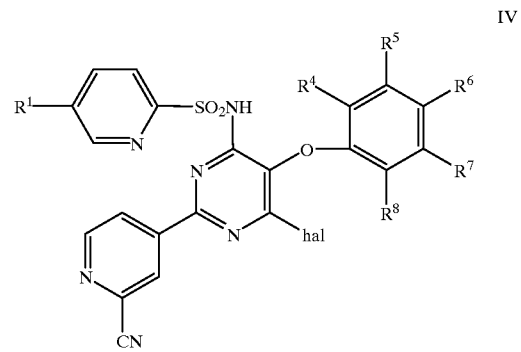

wherein
R$^1$, R$^4$ to R$^8$ and hal are as above
or salts thereof characterized in that the compound of formula III is reacted with a compound of formula V

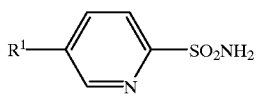

wherein $R^1$ represents lower-alkyl, preferably methyl or isopropyl.

This reaction is carried out by conventional amide formation such as under basic conditions for example in the presence of a coupling agent, e.g. 1,4-diazobicyclo[2.2.2]octane, together with potassium carbonate in acetone.

The compounds of formula IV as defined above may then be converted into the tetrazoles of formula VI above or salts thereof by reacting the compound of formula IV with hydrazine hydrate and a nitrite salt, e.g. an alkali nitrite salt such as sodium nitrite, followed by a reaction under basic conditions with a compound of the formula H—O—C$(R_aR_b)_n$—OR$^9$, wherein $R^9$, $R^{10}$, $R_a$, $R_b$, and n have the significance as defined above.

Alternatively, the compound of formula IV as defined above may be reacted under basic conditions with a compound of the formula H—O—C$(R_aR_b)_n$—OR$^9$, wherein $R^9$, $R^{10}$, $R_a$, $R_b$, and n have the significance as defined above, followed by a reaction with hydrazine hydrate and a nitrite salt as defined above. In the above, the term "basic conditions" means in the presence of a base, preferably in the presence of a metal hydroxide, more preferably in the presence of sodium hydroxide.

This reaction is conveniently carried out by heating, e.g. to 40° C.–100° C., in a glycol corresponding to the compound of the formula H—O—C$(R_aR_b)_n$—OR$^9$ as a solvent, e.g. in ethylene glycol when n=2 and $R_a$ and $R_b$ are hydrogen. $R^3$ is preferably —O(CH$_2$)$_n$OH and n is preferably 2.

Particularly preferred are the above processes wherein $R^1$ is lower alkyl; $R^2$ is tetrazolyl; $R^3$ is 2-hydroxy-ethoxy; $R^4$ to $R^7$ are hydrogen and $R^8$ is lower alkoxy. More particularly preferred is the process wherein $R^1$ is methyl or isopropyl; $R^2$ is tetrazolyl; $R^3$ is 2-hydroxy-ethoxy; $R^4$ to $R^7$ are hydrogen and $R^8$ is methoxy.

A particularly preferred embodiment of the present invention is the process for the preparation of 5-methyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide or salts thereof using the reaction conditions as described above characterized in that the process comprises a) the reaction of 5-(2-methoxy-phenoxy)-2-pyridine-4-yl-pyrimidine-4,6-diole to 4-[4,6-dihydroxy-5-(2-methoxy-phenoxy)-pyrimidine-2-yl]-pyridine-2-carboxylic acid amide as described above;

b) the reaction of 4-[4,6-dihydroxy-5-(2-methoxy-phenoxy)-pyrimidine-2-yl]-pyridine-2-carboxylic acid amide to 4-[4,6-dichloro-5-(2-methoxy-phenoxy)-pyrimidine-2-yl]-pyridine-2-carbonitrile as described above;

c) the reaction of 4-[4,6-dichloro-5-(2-methoxy-phenoxy)-pyrimidine-2-yl]-pyridine-2-carbonitrile to 5-methyl-pyridine-2-sulfonic acid [6-chloro-2-(2-cyano-pyridine-4-yl)-5-(2-methoxy-phenoxy)-pyrimidine-4-yl]-amide as described above;

d) the reaction of 5-methyl-pyridine-2-sulfonic acid [6-chloro-2-(2-cyano-pyridine-4-yl)-5-(2-methoxy-phenoxy)-pyrimidine-4-yl]-amide to 5-methyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide or salts thereof as described above.

Step d) comprises aa) the reaction of 5-methyl-pyridine-2-sulfonic acid [6-chloro-2-(2-cyano-pyridine-4-yl)-5-(2-methoxy-phenoxy)-pyrimidine-4-yl]-amide to 5-methyl-pyridine-2-sulfonic acid [6-chloro-2-[2-(hydrazino-imino-methyl)-pyridine-4-yl]-5-(2-methoxy-phenoxy)-pyrimidine-4-yl]-amide by reaction with hydrazine, followed by conversion of the reaction product to 5-methyl-pyridine-2-sulfonic acid [6-chloro-5-(2-methoxy-phenoxy)-2-[2-(1H-tetrazole-5-yl)-pyridine-4-yl]-pyrimidine-4-yl]-amide or salts thereof by reaction with an alkali nitrite, e.g. sodium nitrite; and bb) the reaction of 5-methyl-pyridine-2-sulfonic acid [6-chloro-5-(2-methoxy-phenoxy)-2-[2-(1H-tetrazole-5-yl)-pyridine-4-yl]-pyrimidine-4-yl]-amide to 5-methyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide or salts thereof by reaction with ethylene glycol;

The sequence of the corresponding reactions of steps aa) and bb) may optionally be exchanged.

Another particularly preferred embodiment of the present invention is the process for the preparation of 5-isopropyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide or salts thereof using the reaction conditions as described above characterized in that the process comprises the steps a) and b) as described above followed by c) the reaction of 4-[4,6-dichloro-5-(2-methoxy-phenoxy)-pyrimidine-2-yl]-pyridine-2-carbonitrile to 5-isopropyl-pyridine-2-sulfonic acid [6-chloro-2-(2-cyano-pyridine-4-yl)-5-(2-methoxy-phenoxy)-pyrimidine-4-yl]-amide as described above;

d) the reaction of 5-isopropyl-pyridine-2-sulfonic acid [6-chloro-2-(2-cyano-pyridine-4-yl)-5-(2-methoxy-phenoxy)-pyrimidine-4-yl]-amide to 5-isopropyl-pyridine-2-sulfonic acid [6-(2-hydroxy-ethoxy)-5-(2-methoxy-phenoxy)-2- [2-(1H-tetrazole-5-yl)-pyridine-4-yl]-pyrimidine-4-yl]-amide or salts thereof as described above.

Step d) comprises aa) the reaction of 5-isopropyl-pyridine-2-sulfonic acid [6-chloro-2-(2-cyano-pyridine-4-yl)-5-(2-methoxy-phenoxy)-pyrimidine-4-yl]-amide to 5-isopropyl-pyridine-2-sulfonic acid [6-chloro-2-[2-(hydrazino-imino-methyl)-pyridine-4-yl]-5-(2-methoxy-phenoxy)-pyrimidine-4-yl]-amide by reaction with hydrazine, followed by conversion of the reaction product to 5-isopropyl-pyridine-2-sulfonic acid [6-chloro-5-(2-methoxy-phenoxy)-2-[2-(1H-tetrazole-5-yl)-pyridine-4-yl]-pyrimidine-4-yl]-amide or salts thereof by reaction with an alkali nitrite, e.g. sodium nitrite; and bb) the reaction of 5-isopropyl-pyridine-2-sulfonic acid [6-chloro-5-(2-methoxy-phenoxy)-2-[2-(1H-tetrazole-5-yl)-pyridine-4-yl]-pyrimidine-4-yl]-amide to 5-isopropyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide or salts thereof by reaction with ethylene glycol;

The sequence of the corresponding reactions of steps aa) and bb) may optionally be exchanged.

Compounds of the formula I and their salts are new and are also part of the present invention:

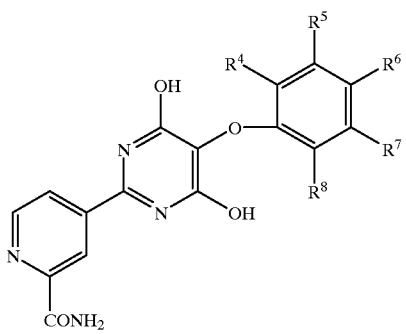

wherein $R^4$ to $R^8$ are as above.

Particularly preferred are the compounds of formula I and salts thereof as defined above wherein $R^4$ to $R^7$ represent hydrogen and $R^8$ represents lower alkoxy. More particularly preferred is 4-[4,6-dihydroxy-5-(2-methoxy-phenoxy)-pyrimidine-2-yl]-pyridine-2-carboxylic acid amide and salts thereof.

Another embodiment of the present invention are compounds of the formula III and their salts:

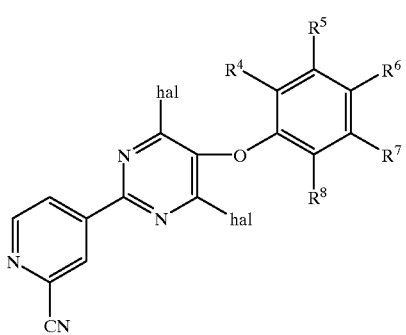

wherein
$R^4$ to $R^8$ and hal are as above.

Particularly preferred are the compounds of formula III and salts thereof as defined above wherein $R^4$ to $R^7$ represent hydrogen, $R^8$ represents lower alkoxy and hal represents chloro. More particularly preferred is 4-[4,6-dichloro-5-(2-methoxy-phenoxy)-pyrimidine-2-yl]-pyridine-2-carbonitrile and salts thereof.

Furthermore, compounds of the formula IV and their salts are new and are also part of the present invention:

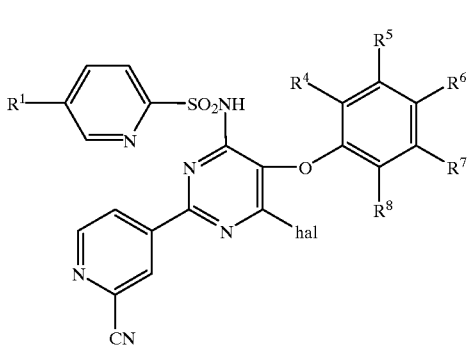

wherein
$R^1$, $R^4$ to $R^8$ and hal are as above.

Particularly preferred are the compounds of formula IV and salts thereof as defined above wherein $R^1$ represents methyl or isopropyl, $R^4$ to $R^7$ represent hydrogen, $R^8$ represents lower alkoxy and hal represents chloro. More particularly preferred are 5-methyl-pyridine-2-sulfonic acid [6-chloro-2-(2-cyano-pyridine-4-yl)-5-(2-methoxy-phenoxy)-pyrimidine-4-yl]-amide and salts thereof as well as 5-isopropyl-pyridine-2-sulfonic acid [6-chloro-2-(2-cyano-pyridine-4-yl)-5-(2-methoxy-phenoxy)-pyrimidine-4-yl ]-amide and salts thereof.

The compounds of formula VI as defined above can be converted in a manner known per se into pharmaceutically acceptable salts. The compounds of formulas I to IV as defined above can be optionally obtained as salts, for example as pharmaceutically acceptable salts, or of course as other salts, which do not necessarily have to be pharmaceutically acceptable.

The compounds which are used as starting materials in the present invention are known from WO 9619459 or can be prepared in analogy to the methods described therein. In principle, the preparation of the starting compounds comprises the reaction of 4-amidino-pyridine hydrochloride with a corresponding dimethyl- or diethyl(2-methoxyphenoxy)malonate.

The following examples shall illustrate preferred embodiments of the present invention but are not intended to limit the scope of the invention.

EXAMPLE 1

1360 ml of formamide were added to 136 g (437 mmol) of 5-(2-methoxy-phenoxy)-2-pyridine-4-yl-pyrimidine-4,6-diole. Then, at a temperature of 0° C., 11.7 ml (219 mmol) of concentrated sulfuric acid and thereafter 36.5 g (130 mmol) of iron(II)sulfate heptahydrate were added to the suspension. After that, 89 ml (874 mmol) of 30% hydrogen peroxide were added dropwise within 1 hr at a temperature of 0° C. to 5° C. The viscous yellow-brownish suspension was stirred at 0° C. for 1.5 hr. Subsequently, a solution of 83 g (437 mmol) of sodium pyrosulfite in 680 ml of de-ionized water was added dropwise to the reaction mixture within 30 min. at 0° C. to 5° C. and the reaction mixture was stirred at 0° C. to 5° C. for 30 min. The suspension was then filtered under reduced pressure. The filtrate was first washed with 1750 ml of de-ionized water and thereafter with 700 ml of ethanol. Then the solid was dried at 80° C., 2000 Pa for 16 hr. There were obtained 132.4 g (91% of theory) of 4-[4,6-dihydroxy -5-(2-methoxy-phenoxy)-pyrimidine-2-yl]-pyridine-2-carboxylic acid amide with a HPLC purity of 91.4% (w/w).

Preparation of Starting Material a) 53.1 g of 4-cyano-pyridine (98%) are added all at once to a solution of 1.15 g of sodium in 200 ml of abs. MeOH. After 6 hr 29.5 g of $NH_4Cl$ are added while stirring vigorously. The mixture is stirred at room temperature overnight. 600 ml of ether are added thereto, whereupon the precipitate is filtered off under suction and thereafter dried at 50° C. under reduced pressure. There is thus obtained 4-amidino-pyridine hydrochloride (decomposition point 245–247° C.).

b) 112.9 g of diethyl (2-methoxyphenoxy)malonate are added dropwise within 30 min. to a solution of 27.60 g of sodium in 400 ml of MeOH. Thereafter, 74.86 g of the amidine hydrochloride obtained in a) are added all at once. The mixture is stirred at room temperature overnight and evaporated at 50° C. under reduced pressure. The residue is treated with 500 ml of ether and filtered off under suction. The filter cake is dissolved in 1000 ml of H$_2$O and treated little by little with 50 ml of CH$_3$COOH. The precipitate is filtered off under suction, washed with 400 ml of H$_2$O and dried at 80° C. under reduced pressure. There is thus obtained 5-(2-methoxy-phenoxy)-2-(pyridine-4-yl)-pyrimidine-4,6-diole (or tautomer), melting point above 250° C.

EXAMPLE 2

Within 20 min. 61 ml (633 mmol) of POCl$_3$ were added dropwise to 34 ml (200 mmol) of diisopropyl ethylamine at 5° C. to 10° C. followed by stirring at 5° C. to 10° C. for 15 min. Then 23.5 g (66 mmol) of 4-[4,6-dihydroxy-5-(2-methoxy-phenoxy)-pyrimidine-2-yl]-pyridine-2-carboxylic acid amide were added in four portions under cooling followed by stirring at 90° C. for 25 hr. The reaction mixture was cooled down to 20° C. and transferred to a new flask together with 50 ml of dichloromethane. Volatile components (i.e. excess of POCl$_3$) was removed by evaporation from 20° C. to 70° C. followed by re-distillation with 100 ml of toluene. After adding 250 ml of dichloromethane to the residue (88 g of a black oil) the solution was heated to 35° C. to 40° C. and 80 ml of de-ionized water were added dropwise within 30 min. whereby the pH was kept constant by the subsequent addition of 28% NaOH solution (60 ml) within 5 to 6 hr. The mixture was stirred at 35° C. to 40° C. for 30 min. followed by removal of dichloromethane by distillation. The resulting suspension was allowed to cool down to 20° C. and was stirred for additional 2 hr. The solid was filtered off under suction, washed with 500 ml of water and dried at 70° C., 2000 Pa for 16 hr. There were obtained 21.3 g (86% of theory) of 4-[4,6-dichloro-5-(2-methoxy-phenoxy)-pyrimidine-2-yl]-pyridine-2-carbonitrile with a HPLC purity of 94.3% (w/w).

EXAMPLE 3

12.5 g (33.5 mmol) of 4-[4,6-dichloro-5-(2-methoxy-phenoxy)-pyrimidine-2-yl]-pyridine-2-carbonitrile and 6.06 g (35 mmol) of 5-methyl-pyridine-2-sulfonamide were added to 130 ml of acetone. 15 g of potassium carbonate and 190 mg (1.6 mmol) of 1,4-diazobicyclo[2.2.2]octane were added and the suspension was stirred at 40° C. for 5 hr and at 20° C. for 15 hr. Then 50 ml of de-ionized water were added followed by dropwise addition of 50 ml of 3 N hydrochloric acid (pH of the solution=1). Acetone was removed by evaporation and the suspension was stirred for 1 hr. The solid was filtered and washed with 100 ml of water. The residue was heated (reflux) in 100 ml of methanol for 1 hr followed by cooling to 20° C. The solid was filtered and dried at 80° C., 2000 Pa for 16 hr. There were obtained 16.0 g (93% of theory) of 5-methyl-pyridine-2-sulfonic acid [6-chloro-2-(2-cyano-pyridine-4-yl)-5-(2-methoxy-phenoxy)-pyrimidine-4-yl]-amide with a HPLC purity of 90.3% (w/w).

EXAMPLE 4

8.95 g (24 mmol) of 4-[4,6-dichloro-5-(2-methoxy-phenoxy)-pyrimidine-2-yl]-pyridine-2-carbonitrile were suspended in 100 ml of acetone. At a temperature of 20° C., 5.04 g (25 mmol) of 5-isopropyl-pyridine-2-sulfonamide, 1 ml of de-ionized water, 10.6 g (77 mmol) of potassium carbonate and 135 mg (1.2 mmol) 1,4-diazobicyclo[2.2.2]octane were added. The mixture was stirred at 40° C. for 20 hr. Thereafter, another 240 mg (1.2 mmol) of 5-isopropyl-pyridine-2-sulfonamide and 80 mg (0.7 mmol) of 1,4-diazobicyclo[2.2.2]octane were added. The reaction mixture was stirred for 24 hr at 40° C. followed by cooling to 20° C. Then 50 ml of de-ionized water and 45 ml of 3 N aqueous hydrochloric acid were added slowly until pH=1. The acetone was removed by distillation and the resulting suspension was stirred at 20° C. for 1.5 hr. The solid was filtered off under suction, washed first with 100 ml of de-ionized water and thereafter with 50 ml of t-butylmethylether. Then the solid was dried at 70° C., 2000 Pa for 20 hr. There were obtained 13.2 g (102% of theory) of 5-isopropyl-pyridin 2-sulfonic acid [6-chloro-2-(2-cyano-pyridine-4-yl)-5-(2-methoxy-phenoxy)-pyrimidine-4-yl]-amide with a HPLC purity of 87.8% (w/w).

EXAMPLE 5

20 g (39 mmol) of 5-methyl-pyridine-2-sulfonic acid [6-chloro-2-(2-cyano-pyridine-4-yl)-5-(2-methoxy-phenoxy)-pyrimidine-4-yl]-amide were suspended in 100 ml of N,N-dimethyl formamide and 7.6 ml (156 mmol) of hydrazine hydrate were added within 15 min. The reaction mixture was allowed to warm up slowly to 20° C. After 17.5 hr, at a temperature of 15° C., 250 ml of de-ionized water were added followed by slow addition of 10.5 ml acetic acid (until pH=5.4). The resulting suspension was stirred for 2 hr at 20° C. and then for additional 2 hr 0° C. The solid was filtered off under suction, firstly washed with 200 ml of de-ionized water and thereafter with 100 ml of t-butylmethylether. The residue was dried at 40° C., 2000 Pa for 18 hr. There were obtained 21.7 g (102% of theory) of 5-methyl-pyridine- 2-sulfonic acid [6-chloro-2-[2-(hydrazino-imino-methyl)-pyridine-4-yl]-5-(2-methoxy-phenoxy)-pyrimidine-4-yl]-amide with a HPLC purity of 81.4% (w/w).

EXAMPLE 6

122 g (233 mmol) of 5-isopropyl-pyridine-2-sulfonic acid [6-chloro-2-(2-cyano-pyridine-4-yl)-5-(2-methoxy-phenoxy)-pyrimidine-4-yl]-amide was suspended in 450 ml of N,N-dimethyl formamide and the mixture was cooled down to 15° C. At this temperature, 35 ml of hydrazine hydrate were added dropwise within 1 hr. The resulting solution was stirred at 15° C. to 20° C. for 16 hr and thereafter diluted with 600 ml of de-ionized water. Then 50 ml of glacial acetic acid were added dropwise at 0° C. to 5° C. until pH=5.5. 600 g of ice were added and the suspension was stirred for 1 hr. The solid was filtered off under suction, washed with 3000 ml of water and dried at 40° C., 2000 Pa for 24 hr. There were obtained 126 g (97% of theory) of 5-isopropyl-pyridine-2-sulfonic acid [6-chloro-2-[2-(hydrazino-imino-methyl)-pyridine-4-yl]-5-(2-methoxy-phenoxy)-pyrimidine-4-yl]-amide with a HPLC purity of 91.8% (w/w).

EXAMPLE 7

20 g (37 mmol) of 5-methyl-pyridine-2-sulfonic acid [6-chloro-2-[2-(hydrazino-imino-methyl)-pyridine-4-yl]-5-(2-methoxy-phenoxy)-pyrimidine-4-yl]-amide were added to 160 ml of N,N-dimethyl formamide. To this solution was added dropwise 23 ml of 6 N aqueous hydrochloric acid at a temperature of 15° C. Then a solution containing 5.1 g (74 mmol) of sodium nitrite in 20 ml de-ionized water was added slowly. The reaction mixture was allowed to warm up to 20° C. and was stirred for 1.5 hr. Then 160 ml of de-ionized water were added and the suspension was stirred for 1 hr. The solid was filtered off under suction, washed with 100 ml of de-ionized water and dried at 50° C., 2000

Pa for 17 hr. There were obtained 18.9 g (92% of theory) of 5-methyl-pyridine-2-sulfonic acid [6-chloro-5-(2-methoxy-phenoxy)-2-[2-(1H-tetrazole-5-yl)-pyridine-4-yl]-pyrimidine-4-yl]-amide with a HPLC purity of 89.6% (w/w).

EXAMPLE 8

20 g (35 mmol) of 5-isopropyl-pyridine-2-sulfonic acid [6-chloro-2-[2-(hydrazino-imino-methyl)-pyridine-4-yl]-5-(2-methoxy-phenoxy)-pyrimidine-4-yl]-amide were added to 160 ml of N,N-dimethyl formamide. The solution was kept at 15° C. to 20° C. and 23 ml of 6 N aqueous hydrochloric acid were added, followed by addition of a solution containing 4.8 g (7 mmol) of sodium nitrite in 20 ml de-ionized water within 10 min. The mixture was stirred at 20° C. for 1 hr, then 140 ml of de-ionized water were added and the suspension was stirred at 0° C. for 1 hr. The solid was filtered, firstly washed with 80 ml of de-ionized water and thereafter with 80 ml of t-butylmethylether. Then the solid was dried at 70° C. and 2000 Pa for 16 hr. The crude product (23.4 g) was taken up with 117 ml of tetrahydrofuran for 1 hr. After filtration at 0° C. the crystallized product was washed with 25 ml of t-butylmethylether and was then dried at 70° C., 2000 Pa for 16 hr. There were obtained 17.3 g (84% of theory) of 5-isopropyl-pyridine-2-sulfonic acid [6-chloro-5-(2-methoxy-phenoxy)-2-[2-(1H-tetrazole-5-yl)-pyridine-4-yl]-pyrimidine-4-yl]-amide with a HPLC purity of 91.1% (w/w).

EXAMPLE 9

15 g (27 mmol) of 5-methyl-pyridine-2-sulfonic acid [6-chloro-5-(2-methoxy-phenoxy)-2-[2-(1H-tetrazole-5-yl)-pyridine-4-yl]-pyrimidine-4-yl]-amide were suspended in 75 ml of ethylene glycol and 6.5 g (163 mmol) of sodium hydroxide were added. The reaction mixture was heated to 85° C. and stirred for 5 hr. Then 55 ml of de-ionized water and thereafter 55 ml of 3 N aqueous hydrochloric acid were added dropwise. The suspension was stirred at 20° C. for 1 hr. The solid was filtered off under suction, washed with 150 ml of de-ionized water and dried at 70° C., 2000 Pa for 17 hr. The crude product (16.4 g) was dissolved in 50 ml of N,N-dimethyl formamide and 40 ml of dioxane at 70° C. Gaseous ammonia was introduced into this solution until pH=9. The resulting suspension was allowed to cool down slowly. The suspension was stirred at 0° C. The solid was filtered off under suction, firstly washed with 25 ml of dioxane and thereafter with 25 ml of ethanol. Then the solid was dried at 50° C., 2000 Pa for 23 hr. The resulting ammonium salt (10.4 g, 17.5 mmol) was suspended in 50 ml of methanol and thereafter 6.5 ml (35 mmol) of a 5.4 N sodium methylate solution were added. The solution was heated (reflux) for 3 hr, cooled down slowly to 20° C. and then to 0° C. The solid was separated by filtering, washed with 10 ml of ice-cold methanol and dried at 70° C., 2000 Pa for 17 hr. There were obtained 6.9 g (41% of theory) of 5-methyl-pyridine-2-sulfonic acid [6-(2-hydroxy-ethoxy)-5-(2-methoxy-phenoxy)-2-[2-( 1H-tetrazole-5-yl)-pyridine-4-yl]-pyrimidine-4-yl]-amide sodium salt (1:2) with a HPLC purity of 98.2% (w/w).

EXAMPLE 10

6.2 g of sodium hydroxide were added to 15 g (26 mmol) of 5-isopropyl-pyridine-2-sulfonic acid [6-chloro-5-(2-methoxy-phenoxy)-2-[2-( 1H-tetrazole-5-yl)-pyridine-4-yl]-pyrimidine-4-yl]-amid and 75 ml of ethylene glycol. The mixture was heated to 85° C. for 5 hr. Then 55 ml of de-ionized water were added and thereafter 55 ml of 3 N hydrochloric acid were added dropwise. The mixture was allowed to cool down to 20° C. and was stirred for 1 hr. The solid was filtered off and dried at 70° C., 2000 Pa for 18 hr. There were obtained 16.2 g (103%) of 5-isopropyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide with a HPLC purity of 92% (w/w). 80 ml of dioxane and 80 ml of ethanol were added to this solid. At a temperature of 60° C., gaseous ammonia was introduced into the liquid until pH=9 to 10. The resulting suspension was allowed to cool down to 20° C. and was stirred at 20° C. for 20 hr and thereafter at 0° C. for 2.5 hr. Then the solid was filtered off and dried at 70° C., 2000 Pa for 18 hr. There were obtained 14.2 g of mono ammonium salt with a HPLC purity of 96.2% (w/w). The solid was heated (reflux) in 70 ml of methanol, cooled down slowly to 20° C. and stirred at 20° C. for 19 hr and thereafter at 0° C. for 2 hr. Then the solid was filtered off and dried at 70° C., 2000 Pa for 19 hr. There were obtained 11.5 g (66% of theory) of 5-isopropyl-pyridine-2-sulfonic acid [6-(2-hydroxy-ethoxy)-5-(2-methoxy-phenoxy)-2-[2-(1H-tetrazole-5-yl)-pyridine-4-yl]-pyrimidine-4-yl]-amide sodium salt (1:2) with a HPLC purity of 98.6% (w/w).

What is claimed is:

1. A process for the producing an amide selected from a compound of the formula

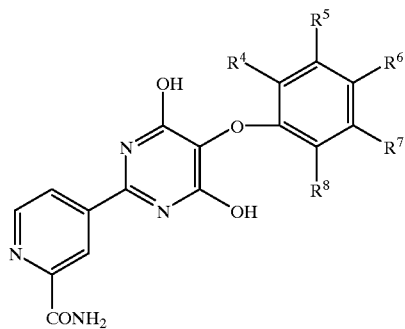

I wherein $R^4$ through $R^8$ are each independently hydrogen, lower-alkoxy or halogen;
and a salt thereof; comprising reacting a compound of the formula

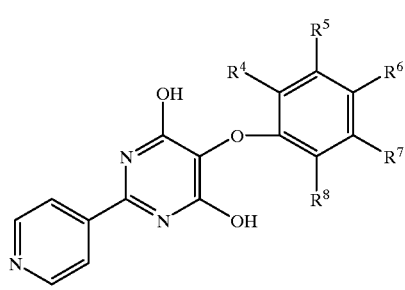

II wherein $R^4$ through $R^8$ are as above;
or a salt thereof with formamide and an oxidizing agent in an aqueous acidic solution, to produce said amide, said reaction being carried out in the presence of 15 to 40 mole % of an ionic Fe (II) salt, said mole % being based upon the moles of said compound of formula II in the reaction.

2. The process of claim 1, wherein the ionic Fe (II) salt is a salt of Fe II with an anion selected from the group consisting of chloride, bromide, sulfate, phosphate, tetrafluoroborate and hexafluoroborate.

3. The process of claim 1, wherein the reaction is carried out at a temperature from 0° C. to 35° C.

4. The process of claim 1, wherein the reaction is carried out in the presence of 20 to 30 mole % of said ionic Fe (II) salt based upon the moles of compound II in the reaction.

5. The process of claim 1, wherein the oxidizing agent is hydrogen peroxide.

6. A process for the preparation of a cyanide selected from the group consisting of a compound of the formula

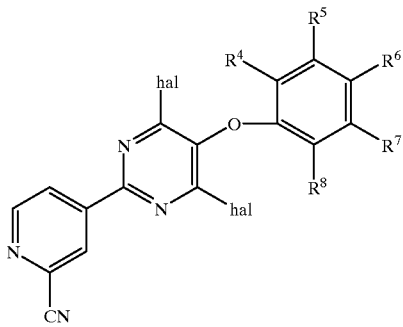

III wherein $R^4$ to $R^8$ are each independently hydrogen, lower alkoxy or halogen;
hal is halogen;

and a pharmaceutically acceptable salt comprising:

a) reacting a compound of the formula

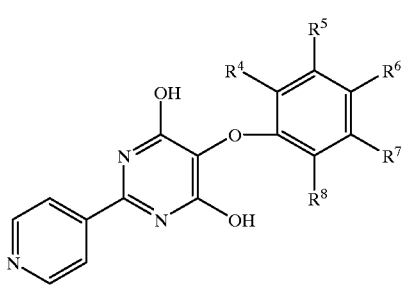

II wherein $R^4$ through $R^8$ are as above, or a salt thereof with formamide and an oxidizing agent in an aqueous acidic solution, to produce an amide selected from the group consisting of compounds of the formula

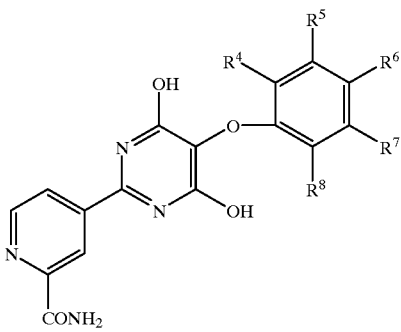

I wherein $R^4$ to $R^8$ are as above,
said reaction being carried out in the presence of 15 to 40 mole % of an ionic Fe (II) salt, said mole % being based upon the moles of said compound of formula II in the reaction; and
b) converting said amide to a cyanide selected from the group consisting of a compound of the formula

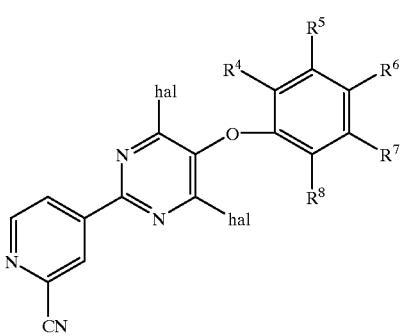

III wherein $R^4$ to $R^8$ are as above;
hal is a halogen; and
and salts thereof,
by treating said amide with a halogenating agent capable of removing water in the presence of a base.

7. The process of claim 6, wherein said halogenating agent is PO(hal)$_3$, P(hal)$_5$, or SO(hal)$_2$ and hal is as above.

8. The process of claim 7, wherein said agent is POCl$_3$.

9. A process of producing a sulfonic acid amide selected from the group consisting of a compound of the formula

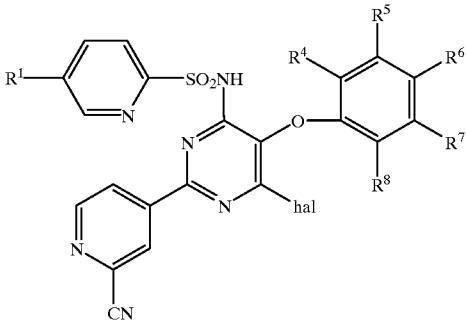

IV wherein $R_1$ is lower alkyl;
$R^4$ to $R^8$ are each individually hydrogen, lower alkoxy or halogen;
and hal is halogen;

and a salt thereof comprising:

a) reacting a compound of the formula

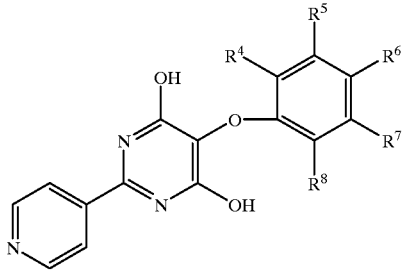

II wherein $R^4$ to $R^8$ are as above, or a salt thereof with formamide and an oxidizing agent in an aqueous acidic solution, to produce an amide selected from the group consisting of compounds of the formula

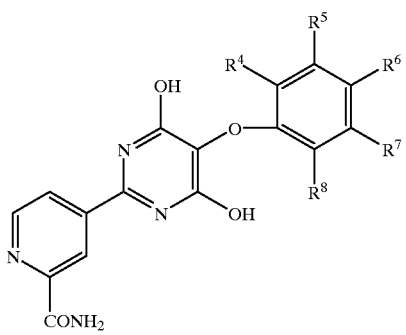

I wherein $R^4$ to $R^8$ are as above,
and salts thereof,
said reaction being carried out in the presence of 15 to 40 mole % of a Fe (II) salt, said mole % being based upon the moles of said compound of formula II in the reaction;

b) converting said amide of formula II to a cyanide selected from the group consisting of a compound of the formula

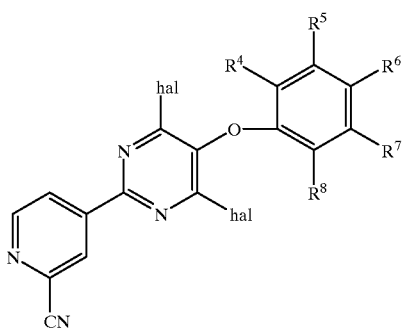

III wherein $R^4$ to $R^8$ are as above; and
hal is a halogen;
and salts thereof,
by treating said amide with a halogenating agent capable of removing water in the presence of a base; and c) reacting said cyanide with a compound of the formula

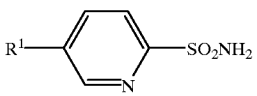

V wherein $R^1$ is lower alkyl to produce said sulfonic acid amide.

10. A process for producing a tetrazole selected from the group consisting of compounds of the formula.

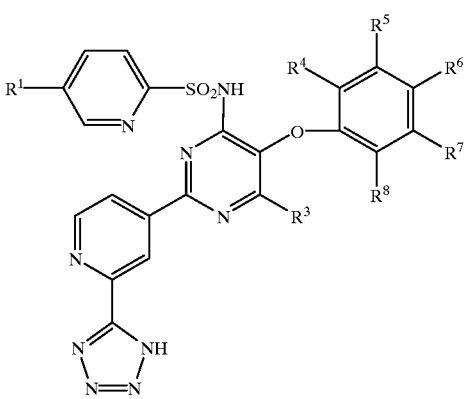

VI wherein
$R^1$ is lower-alkyl;
$R^3$ is —O—$(CR_aR_b)_n$—$OR^9$;
$R^4$ to $R^8$ are each individually hydrogen, lower-alkoxy or halogen;
$R^9$ is hydrogen, aryl, lower-aralkyl, heterocyclyl or a residue —C(O)$NHR^{10}$;
$R^{10}$ is lower-alkyl, phenyl, substituted phenyl, pyridyl or substituted pyridyl;
$R_a$ and $R_b$ are each independently hydrogen or lower-alkyl; and
n is 2, 3 or 4;
and a salt thereof, comprising a) reacting a compound of the formula

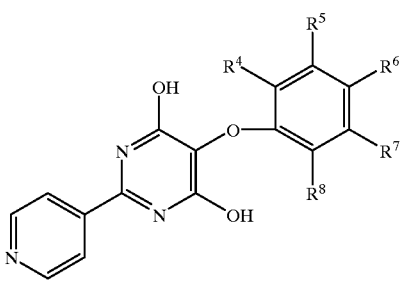

II wherein $R^4$ to $R^8$ are as above, or a salt thereof with formamide and an oxidizing agent in an aqueous acidic solution, to produce an amide selected from the group consisting of compounds of the formula

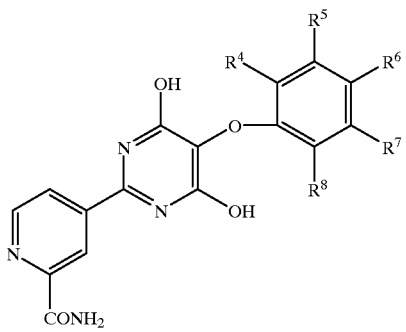

I wherein $R^4$ to $R^8$ are as above, and salts thereof, in the presence of 15 to 40 mole % of an ionic Fe (II) salt, said mole % being based upon the moles of said compound of formula II in the reaction;

b) converting said amide of formula II to a cyanide selected from the group consisting of a compound of formula

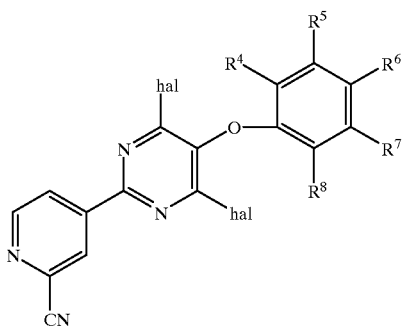

III wherein $R^4$ to $R^8$ are as above; and
hal is a halogen, and salts thereof, by treating said amide with a halogenating agent capable of removing water in the presence of a base;

c) reacting said cyanide with a compound of the formula

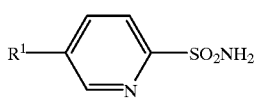

V wherein $R^1$ is lower alkyl to produce a sulfonic acid amide selected from the group consisting of a compound of the formula

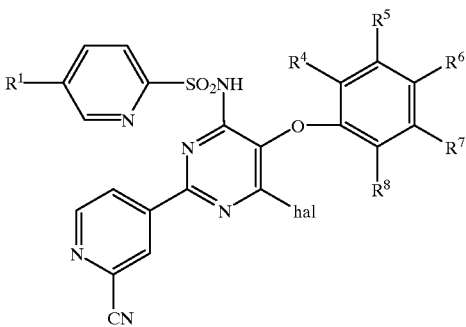

IV wherein $R^1$ is lower alkyl;
$R^4$ to $R^8$ are each individually hydrogen, lower alkoxy or halogen;
and hal is halogen;

and a salt thereof, d) and reacting said sulfonic acid amide with hydrazine hydrate and a nitrite salt followed by a reaction under basic conditions with a compound of the formula

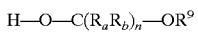

wherein $R^9$, $R^{10}$, $R_a$, $R_b$, and n are as above to produce said tetrazole.

11. A process for producing a tetrazole select from the group consisting of compounds of the formula

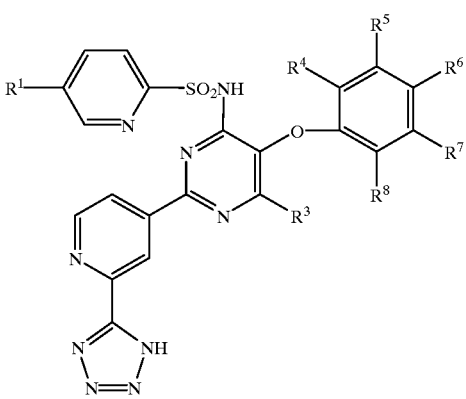

VI wherein
$R^1$ is lower-alkyl;
$R^3$ is $-O-(CR_aR_b)_n-OR^9$;
$R^4$ to $R^8$ are each individually hydrogen, lower-alkoxy or halogen;
$R^9$ is hydrogen, aryl, lower-aralkyl, heterocyclyl or a residue $-C(O)NHR^{10}$;
$R^{10}$ is lower-alkyl, phenyl, substituted phenyl, pyridyl or substituted pyridyl;
$R_a$ and $R_b$ are each independently hydrogen or lower-alkyl; and
n is 2, 3 or 4;

and salts thereof comprising a) reacting a compound of the formula

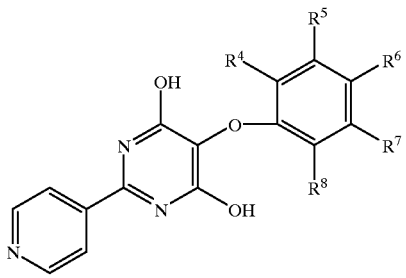

II wherein $R^4$ to $R^8$ are as above, or a salt thereof with formamide and an oxidizing agent in an aqueous acidic solution, to produce an amide selected from the group consisting of compounds of the formula

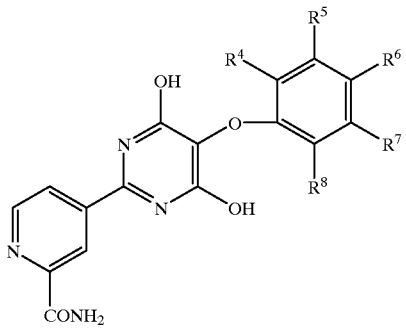

I wherein $R^4$ to $R^8$ are as above,
and salts thereof, said reaction being carried out in the presence of 15 to 40 mole % of an ionic Fe (II) salt, said mole % being based upon the moles of said compound of formula II in the reaction;

b) converting said amide of formula II to a cyanamide selected from the group consisting of a compound of formula

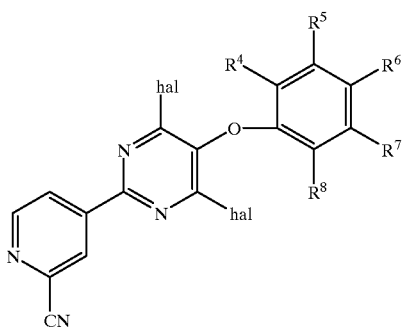

III wherein $R^4$ to $R^8$ are as above; and
hal is a halogen, and salts thereof,
by treating said amide with a halogenating agent capable of removing water in the presence of a base;

c) reacting said cyanide with a compound of the formula

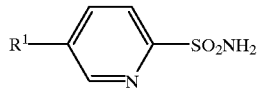

V wherein $R^1$ is lower alkyl
to produce said sulfonic acid amide selected from the group consisting of a compound of the formula

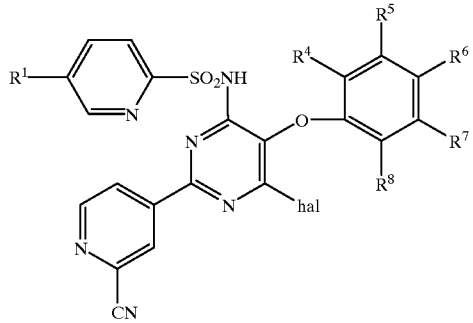

IV wherein $R^1$ is lower alkyl;
$R^4$ to $R^8$ are each individually hydrogen, lower alkoxy or halogen;
and hal is halogen;
and a salt thereof;

d) and reacting said sulfonic acid amide with a compound of the formula

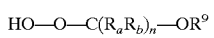

HO—O—C($R_a R_b$)$_n$—OR$^9$ wherein $R^9$, $R^{10}$, $R_a$, $R_b$, and n are as above, followed by reaction with hydrazine hydrate and a nitrite salt to produce said tetrazole.

12. An amide selected from the group consisting of a compound of the formula

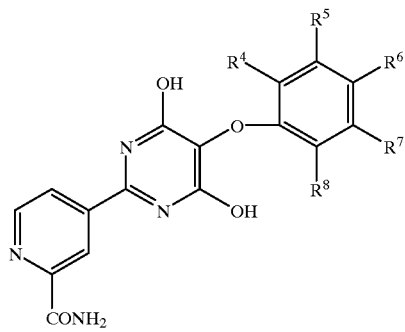

I wherein $R^4$ to $R^8$ are each individually hydrogen, lower-alkoxy or halogen, and a salt thereof.

13. The amide of claim 12 wherein said compound is 4-[4,6-dihydroxy-5-(2-methoxy-phenoxy)-pyrimidine-2-yl]-pyridine-2-carboxylic acid amide.

14. The amide of claim 12 wherein said compound is 4-[4,6-dihydroxy-5-(2-methoxy-phenoxy)-pyrimidine-2-yl]-pyridine-2-carboxylic acid amide.

15. A cyano halide selected from the group consisting of a compound of the formula

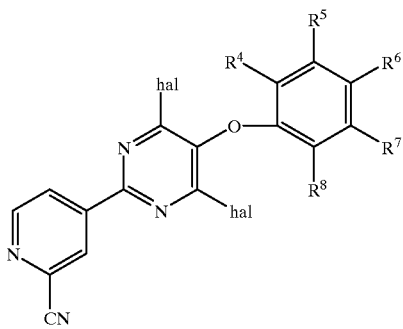

III wherein $R^4$ to $R^8$ are each individually hydrogen, lower-alkoxy or halogen; and hal is halogen and a salt thereof.

16. The cyano halide of claim 13 wherein said compound is 4-[4,6-dichloro-5-(2-methoxy-phenoxy)-pyrimidine-2-yl]-pyridine-2-carbonitrile.

17. The cyano halide of claim 13 wherein said compound is 4-[4,6-dichloro-5-(2-methoxy-phenoxy)-pyrimidine-2-yl]-pyridine-2-carbonitrile.

18. A sulfonic acid amide selected from the group consisting of compounds of the formula

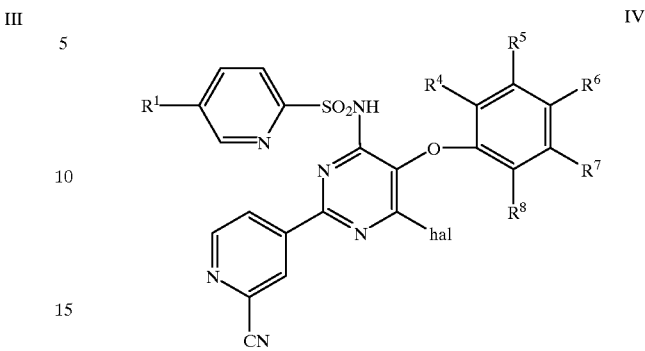

IV wherein
$R^1$ is lower-alkyl;
$R^4$ to $R^8$ are each individually hydrogen, lower-alkoxy or halogen; and
hal is halogen
or a salt thereof.

19. The sulfonic acid of claim 18 wherein said compound of the formula IV is 5-methyl-pyridine-2-sulfonic acid [6-chloro-2-(2-cyano-pyridine-4-yl)-5-(2-methoxy-phenoxy)-pyrimidine-4-yl]-amide.

* * * * *